(12) United States Patent  
Geddis et al.

(10) Patent No.: US 7,794,146 B1  
(45) Date of Patent: Sep. 14, 2010

(54) ULTRASONIC CLEANING POUCH SYSTEM

(76) Inventors: Cheryl J. Geddis, 2221 Paddock Cir., Dunedin, FL (US) 34698; David B. Geddis, 2221 Paddock Cir., Dunedin, FL (US) 34698

( * ) Notice: Subject to any disclaimer, the term of this patent is extended or adjusted under 35 U.S.C. 154(b) by 170 days.

(21) Appl. No.: 12/313,078

(22) Filed: Nov. 17, 2008

(51) Int. Cl.
  B65D 33/06 (2006.01)
  B65D 33/24 (2006.01)
  B65D 33/00 (2006.01)
  B65D 30/00 (2006.01)
  B65D 30/04 (2006.01)

(52) U.S. Cl. .............................. 383/6; 383/86; 383/97; 383/107; 383/117

(58) Field of Classification Search .............. 383/117, 383/97, 107, 86, 6  
See application file for complete search history.

(56) References Cited

U.S. PATENT DOCUMENTS

| | | | | |
|---|---|---|---|---|
| 4,631,211 A | * | 12/1986 | Houghten | 506/30 |
| 4,989,995 A | * | 2/1991 | Rubenstein et al. | 383/117 |
| 5,490,596 A | * | 2/1996 | Katz | 206/439 |
| 5,630,436 A | | 5/1997 | Chase | |
| 6,080,361 A | | 6/2000 | Borovsky | |
| 6,354,312 B1 | | 3/2002 | Lin | |

* cited by examiner

*Primary Examiner*—Jes F Pascua

(57) ABSTRACT

A sheet of material in a generally rectangular configuration has first and second side edges and first and second end edges. The first and second end edges define an opening. A fold between the end edges forms panels with a chamber formed between the panels. Coupling components couple the panels of the sheet to form a pouch. A fastener separably couples the first and second end edges.

9 Claims, 3 Drawing Sheets

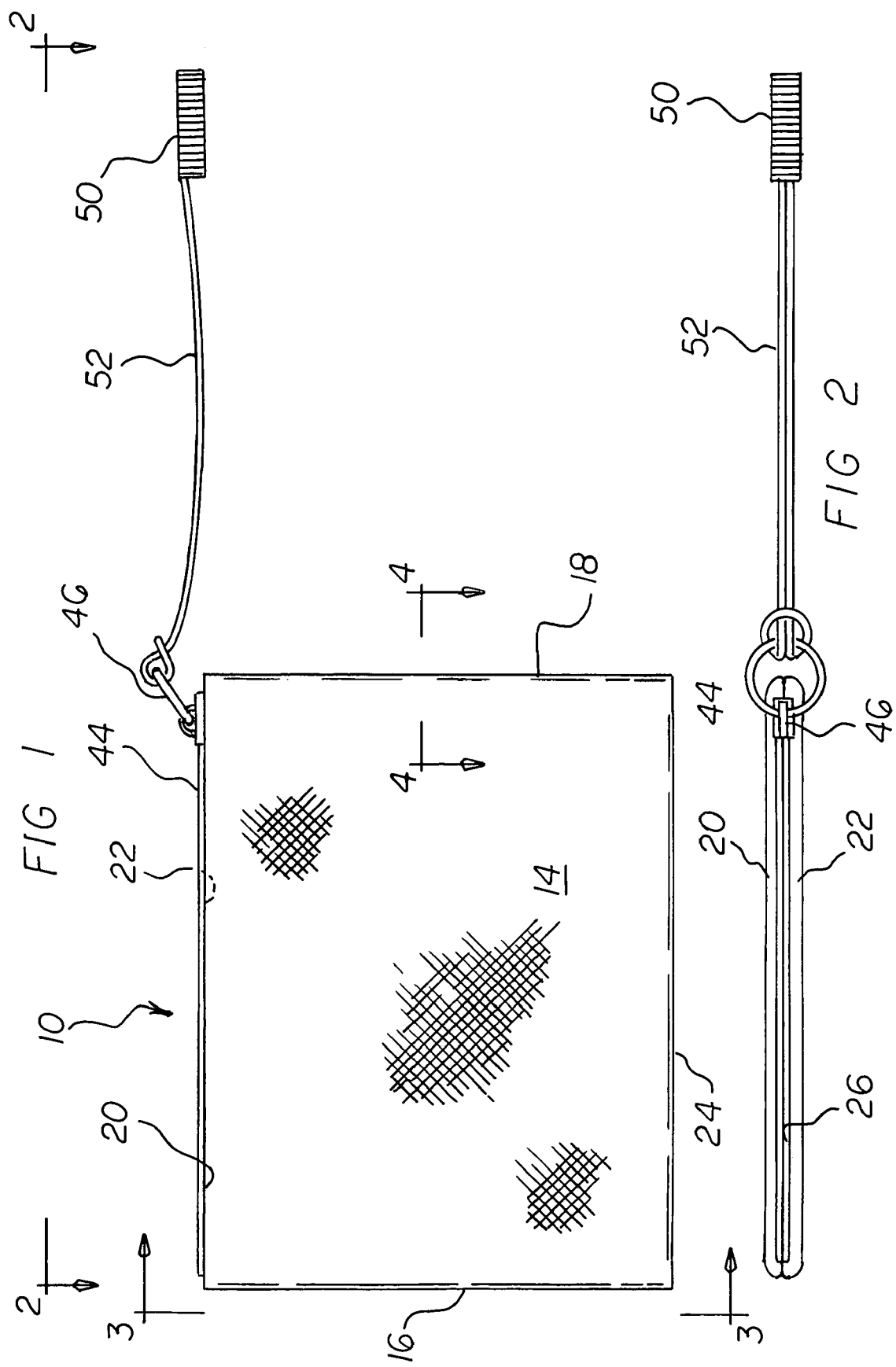

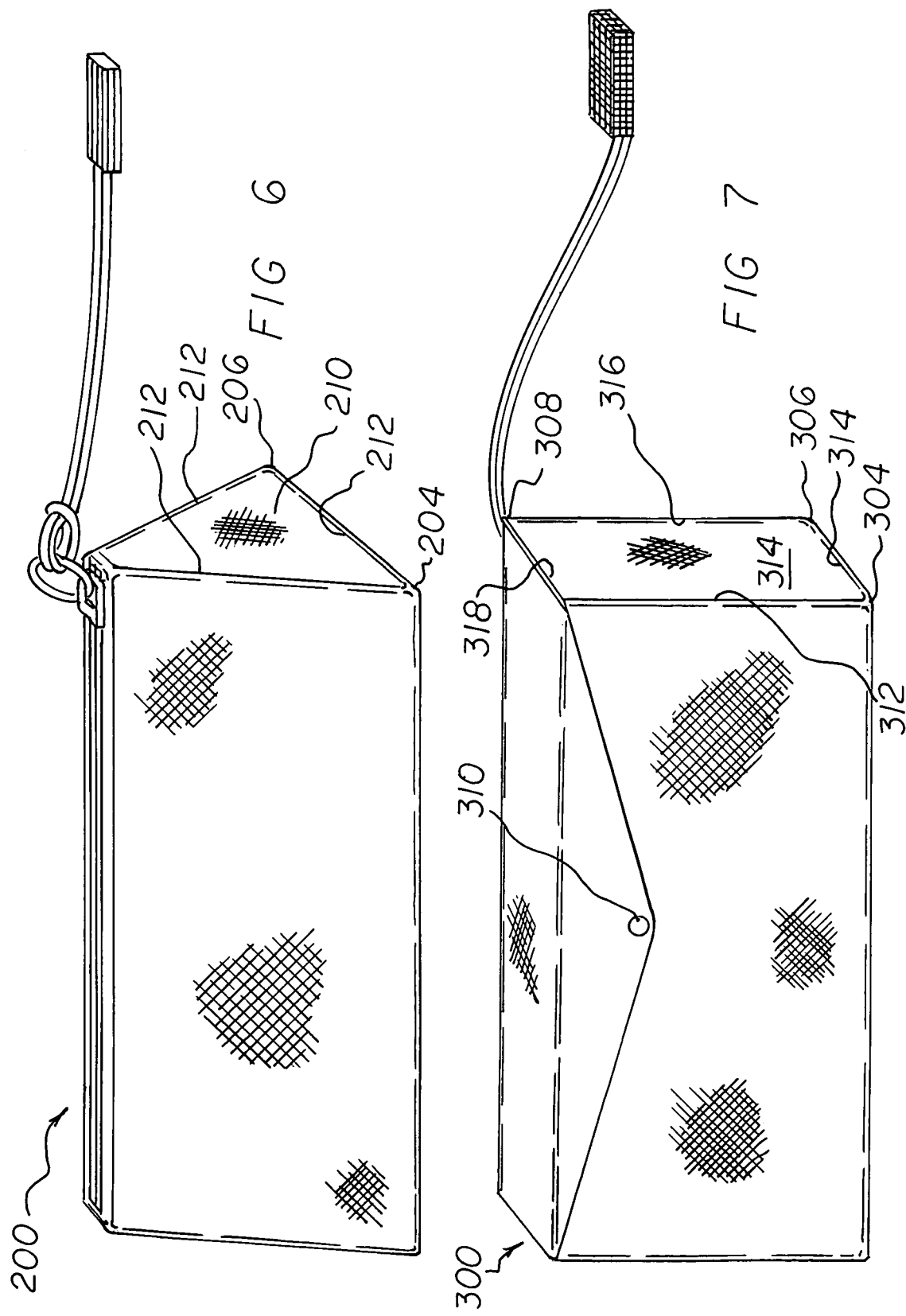

ULTRASONIC CLEANING POUCH SYSTEM

BACKGROUND OF THE INVENTION

1. Field of the Invention

The present invention relates to an ultrasonic cleaning pouch system and more particularly pertains to supporting objects including surgical and non-surgical tools, parts and instruments for pre-soak and ultrasonic cleaning in a water with radio waves, the supporting being done in a safe, convenient and economical manner.

2. Description of the Prior Art

The use of ultrasonic cleaning support devices of known designs and configurations is known in the prior art. More specifically, ultrasonic cleaning support devices of known designs and configurations previously devised and utilized for the purpose of supporting objects for ultrasonic cleaning are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,630,436 issued May 20, 1997 to Chase relates to an Apparatus for Cleaning Long Tubular Medical Instruments. U.S. Pat. No. 6,080,361 issued Jun. 27, 2000 to Borovsky relates to a Contact Lens Cleaning and Disinfection System. Lastly, U.S. Pat. No. 6,354,312 issued Mar. 12, 2002 to Lin relates to a Connector without Occlusion.

While these devices fulfill their respective, particular objectives and requirements, the aforementioned patents do not describe an ultrasonic cleaning pouch system that allows for supporting objects including surgical and non-surgical tools, parts and instruments for pre-soak and ultrasonic cleaning in a water with radio waves, the supporting being done in a safe, convenient and economical manner.

In this respect, the ultrasonic cleaning pouch system according to the present invention substantially departs from the conventional concepts and designs of the prior art, and in doing so provides an apparatus primarily developed for the purpose of supporting objects including surgical and non-surgical tools, parts and instruments for pre-soak and ultrasonic cleaning in a water with radio waves, the supporting being done in a safe, convenient and economical manner.

Therefore, it can be appreciated that there exists a continuing need for a new and improved ultrasonic cleaning pouch system which can be used for supporting objects including surgical and non-surgical tools, parts and instruments for pre-soak and ultrasonic cleaning in a water with radio waves, the supporting being done in a safe, convenient and economical manner. In this regard, the present invention substantially fulfills this need.

SUMMARY OF THE INVENTION

In view of the foregoing disadvantages inherent in the known types of ultrasonic cleaning support devices of known designs and configurations now present in the prior art, the present invention provides an improved ultrasonic cleaning pouch system. As such, the general purpose of the present invention, which will be described subsequently in greater detail, is to provide a new and improved ultrasonic cleaning pouch system and method which has all the advantages of the prior art and none of the disadvantages.

To attain this, the present invention essentially comprises an ultrasonic cleaning pouch system. First provide is a sheet of material in a rectangular configuration. The sheet has a linear first side edge and a linear second side edge. The first and second side edges are vertically oriented and parallel with respect to each other. The sheet also has a linear first end edge and a linear second end edge. The first and second end edges are horizontally oriented and parallel with respect to each other. A fold line is provided midway between the first and second end edges. The first and second end edges are positioned laterally offset from each other and define an opening between the first and second side edges. The fold line divides the sheet into a front panel and a superposed rear panel. A chamber is formed between the front and rear panels for the receipt of surgical instruments to be cleaned through immersion in a fluid medium with ultrasonic waves. The fluid medium in the preferred embodiment is water.

Next provided is a primary row of stitching coupling the front and rear panels parallel with and adjacent to each side edge to form a pouch. The primary row of stitching is formed when the pouch is inverted to be inside out. A secondary row of stitching is formed when the pouch is reverted. Each secondary row of stitching is parallel with and adjacent to an associated primary row of stitching. Each secondary row of stitching is inboard of an associated side edge and an associated primary row of stitching to form a tunnel for an associated side edge and an associated primary row of stitching.

A sliding fastener is next provided. The sliding fastener separably couples the first and second end edges. The sliding fastener has a slider movable between an open position for allowing objects to be inserted into the chamber and a closed position for securing objects in the chamber during ultrasonic cleaning. The preferred sliding fastener is one of the type having plastic edges to be coupled and uncoupled in association with a plastic sliding component to join and separate the plastic edges.

Next provided is a float. The float is fabricated of a buoyant material. A cord couples the float to the slider. The cord and float are adapted to assist a user in retrieving the pouch in the event that the float falls into a fluid medium in which the pouch is being cleaned. The cord is fabricated of a color corresponding to the type of objects in the pouch being cleaned.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ultrasonic cleaning pouch system which has all of the advantages of the prior art ultrasonic cleaning support devices of known designs and configurations and none of the disadvantages.

It is another object of the present invention to provide a new and improved ultrasonic cleaning pouch system which may be easily and efficiently manufactured and marketed.

It is a further object of the present invention to provide a new and improved ultrasonic cleaning pouch system which is of durable and reliable constructions.

An even further object of the present invention is to provide a new and improved ultrasonic cleaning pouch system which is susceptible of a low cost of manufacture with regard to both materials and labor, and which accordingly is then susceptible of low prices of sale to the consuming public, thereby making such ultrasonic cleaning pouch system economically available to buyers.

Even still another object of the present invention is to provide an ultrasonic cleaning pouch system for supporting objects including surgical and non-surgical tools, parts and instruments for pre-soak and ultrasonic cleaning in a water with radio waves, the supporting being done in a safe, convenient and economical manner.

Lastly, it is an object of the present invention to provide a new and improved ultrasonic cleaning pouch system. A sheet of material in a generally rectangular configuration has first and second side edges and first and second end edges. The first and second end edges define an opening. A fold between the end edges forms panels with a chamber formed between the panels. Coupling components couple the panels of the sheet to form a pouch. A fastener separably couples the first and second end edges.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of an ultrasonic cleaning pouch system constructed in accordance with the principles of the present invention.

FIG. 2 is a plan view of the system taken along line 2-2 of FIG. 1.

FIGS. 6 and 7 are perspective illustrations of alternate embodiments of the invention.

The same reference numerals refer to the same parts throughout the various Figures.

DESCRIPTION OF THE PREFERRED EMBODIMENT

Figure 3:
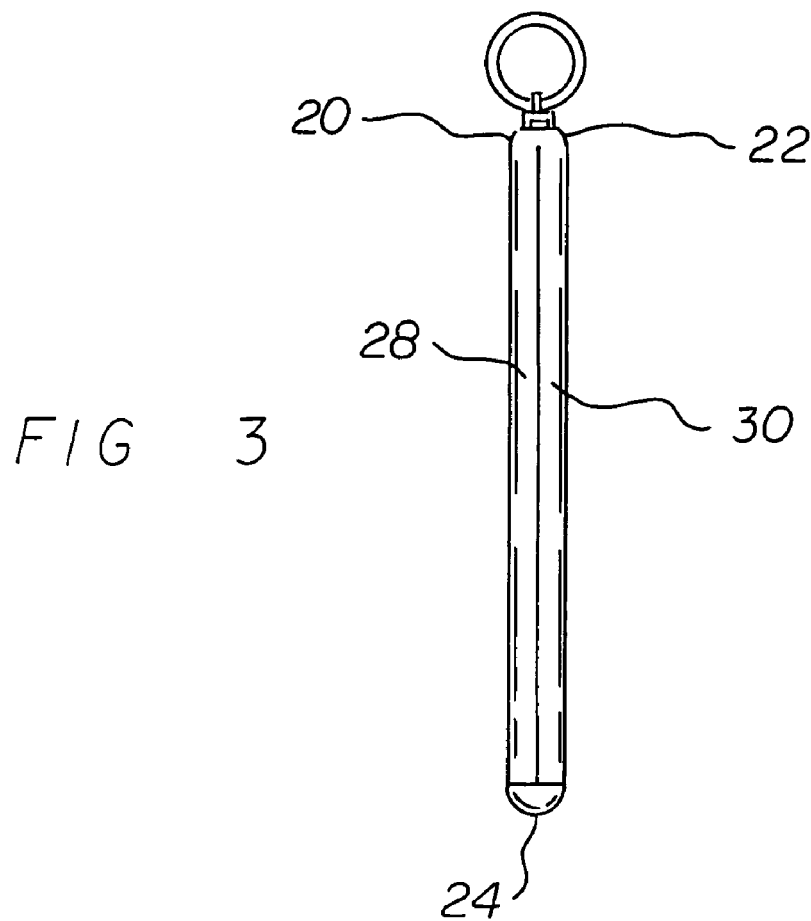
FIG. 3 is a plan view of the system taken along line 3-3 of FIG. 1.
Figure 4:
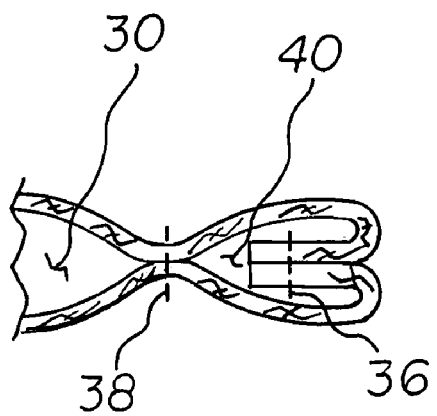
FIG. 4 is a cross sectional view of the system taken along line 4-4 of FIG. 1.

With reference now to the drawings, and in particular to FIG. 1 thereof, the preferred embodiment of the new and improved ultrasonic cleaning pouch system embodying the principles and concepts of the present invention and generally designated by the reference numeral 10 will be described.

The present invention, the ultrasonic cleaning pouch system 10 is comprised of a plurality of components. Such components in their broadest context include a sheet of material, coupling components, and a fastener. Such components are individually configured and correlated with respect to each other so as to attain the desired objective.

First provide is a sheet of material 14 in a rectangular configuration. The sheet has a linear first side edge 16 and a linear second side edge 18. The first and second side edges are vertically oriented and parallel with respect to each other. The sheet also has a linear first end edge 20 and a linear second end edge 22. The first and second end edges are horizontally oriented and parallel with respect to each other. A fold line 24 is provided midway between the first and second end edges. The first and second end edges are positioned laterally offset from each other and define an opening 26 between the first and second side edges. The fold line divides the sheet into a front panel 28 and a superposed rear panel 30. A chamber 32 is formed between the front and rear panels for the receipt of surgical instruments to be cleaned through immersion in a fluid medium with ultrasonic waves. The fluid medium in the preferred embodiment is water.

Next provided is a primary row of stitching 36 coupling the front and rear panels parallel with and adjacent to each side edge to form a pouch. The primary row of stitching is formed when the pouch is inverted to be inside out. A secondary row of stitching 38 is formed when the pouch is reverted. Each secondary row of stitching is parallel with and adjacent to an associated primary row of stitching. Each secondary row of stitching is inboard of an associated side edge and an associated primary row of stitching to form a tunnel 40 for an associated side edge and an associated primary row of stitching.

A sliding fastener 44 is next provided. The sliding fastener separably couples the first and second end edges. The sliding fastener has a slider 46 movable between an open position for allowing objects to be inserted into the chamber and a closed position for securing objects in the chamber during ultrasonic cleaning. The preferred sliding fastener is one of the type having plastic edges to be coupled and uncoupled in association with a plastic sliding component to join and separate the plastic edges.

Next provided is a float 50. The float is fabricated of a buoyant material. A cord 52 couples the float to the slider. The cord and float are adapted to assist a user in retrieving the pouch in the event that the float falls into a fluid medium in which the pouch is being cleaned. The cord is fabricated of a color corresponding to the type of objects in the pouch being cleaned.

In the primary embodiment, the sheet is fabricated of stainless steel threads. Each thread has a diameter of 0.0014 inches, plus or minus 20 percent. The threads are woven with 325 square interstices per square inch, plus or minus 20 percent. The stitching is done with stainless steel threads having a diameter of 0.0014 inches, plus or minus 20 percent.

Figure 5:
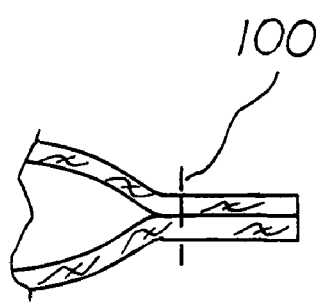
FIG. 5 is a cross sectional view of the seam similar to FIG. 4 but illustrating an alternate embodiment of the invention.

An alternate embodiment of the invention is shown in FIG. 5. In this embodiment, the coupling components include a single row of stitching 100 along each side edge.

Another alternate embodiment of the invention is shown in FIG. 6. In this embodiment of the system 200, the fold includes two parallel fold lines 204, 206 between the end edges. A triangular panel 210 at each end of the pouch has three sides 212 attached to an associated side edge to form a chamber with an enlarged bottom remote from the fastener.

Still another embodiment of the invention is shown in FIG. 7. In this embodiment of the system 300 the fold includes three parallel fold lines 304, 306, 308 between the end edges. The fastener is a snap fastener 310. A rectangular panel 314 at each end of the pouch has four sides 312, 314, 316, 318. Three sides 312, 314, and 316 are attached to an associated side edge to form a chamber with a rectilinear configuration.

When cleaning surgical instruments, and/or other non-surgical items, the general procedure is to place the instruments in a tank containing water and an enzyme detergent solution. This is called presoak cleaning designed to loosen debris. Following the presoak stage, the instruments are then placed in a metal tray or basket which is then placed into an ultrasonic tank containing a water/enzyme solution. The ultrasonic tank is then turned on for a period of 30 to 60 minutes. Ultrasonic cleaning action is created by sound waves beyond the range of the human ear. These sound waves create a scrubbing action by forming millions of microscopic bubbles which blast soils from the surface of the items being cleaned. This is known as cavitations.

The present invention is a semi-disposable, ultrasonic cleaning pouch which can supplement or replace the need for more expensive metal instrument baskets or trays as a container for instruments being cleaned in ultrasonic cleaning machines.

The present invention increases ultrasonic cleaning action. Heavy metal trays and baskets dampen ultrasonic action because of the amount of metal in a basket or tray. The pouch material greatly reduces the amount of ultrasonic wave interference associated with heavier metal containers.

The present invention provides a light weight container for easy instrument transfer. It can be used as a lightweight container to hold instruments in the presoak tank rather than a heavy tray. It is an easy to use lightweight container for transfer of instruments from the presoak tank to the ultrasonic tank.

The present invention reduces costs from losing instruments. Small instruments are often lost down the drain of an ultrasonic tank. The subject pouch encapsulates the small instruments in the pouch eliminating the chance of instruments being lost in an ultrasonic tank when it is drained.

The present invention allows for categorizing instruments by instrument type. Instruments can be categorized in color coded pouches for easy separation after ultrasonic cleaning, for example, scissors in a green pouch, hemostats in a blue pouch.

The present invention helps to reduce injury to hospital staff. Multiple pouches may be used in place of heavy, overloaded, trays or baskets which will decrease the amount of weight being lifted at any one time.

The pouch is made from liquid permeable micro-mesh stainless steel and various other plastic and cloth materials. The pouch material permits easy penetration of ultrasonic sound waves known as cavitations through the pouch material. The pouch is color-coded for easy identification and separation of instrument types. The pouch material is very malleable and can be turned inside out for easy rinsing. The pouch contains a strap to drape over the edge of an ultrasonic tank for easy retrieval of the pouch without having a user place hands into the ultrasonic bath solution. The pouch contains a float on the end of the strap. Should the pouch strap fall into the ultrasonic bath, this float keeps the strap floating on top of the ultrasonic bath for easy retrieval. The pouch may have various closures such as a zipper, snap, Velcro, folds, etc. to contain items being cleaned. The pouch is made in various sizes to accommodate a variety of instrument sizes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ultrasonic cleaning pouch system comprising:
a sheet of material in a generally rectangular configuration, the sheet having first and second side edges, the sheet having first and second end edges, a fold between the end edges, the first and second end edges defining an opening, the fold forming panels with a chamber formed between the panels;
coupling components coupling the panels of the sheet to form a pouch;
a fastener separably coupling the first and second end edges and the sheet is fabricated of stainless steel threads, each thread having a diameter of 0.0014 inches in diameter, plus or minus 20 percent, the threads being woven with 325 square interstices per square inch, plus or minus 20 percent.

2. The system as set forth in claim 1 and further including:
a float fabricated of a buoyant material with a cord coupling the float to the pouch, the cord and the float adapted to assist a user in retrieving the pouch in the event that the float falls into the fluid medium in which the pouch is being cleaned.

3. The system as set forth in claim 2 wherein the cord is fabricated of a color corresponding to the type of objects in the pouch being cleaned.

4. The system as set forth in claim 1 wherein the coupling components include a primary row of stitching coupling the front and rear panels parallel with and adjacent to each side edge to form a pouch, the primary rows of stitching being formed when the pouch is inverted to be inside out, a secondary row of stitching formed when the pouch is reverted, each secondary row of stitching being parallel with and adjacent to an associated primary row of stitching, each secondary row of stitching being inboard of an associated side edge and an associated primary row of stitching to form a tunnel for an associated side edge and an associated primary row of stitching.

5. The system as set forth in claim 1 wherein the fold is a single fold line midway between the first and second end edges.

6. The system as set forth in claim 1 wherein the coupling components include a single row of stitching along each side edge, the stitching being done with stainless steel threads having a diameter of 0.0014 inches in diameter, plus or minus 20 percent.

7. The system as set forth in claim 1 wherein:
the fold includes two parallel fold lines between the end edges; and
the system further includes a triangular panel at each end of the pouch, each triangular panel having three sides attached to an associated side edge to form a chamber with an enlarged bottom remote from the fastener.

8. The system as set forth in claim 1 wherein:
the fold includes three parallel fold lines between the end edges;
the fastener is a snap fastener; and
the system further includes a rectangular panel at each end of the pouch, each rectangular panel having four sides, three sides of which are attached to an associated side edge to form a chamber with a rectilinear configuration.

9. An ultrasonic cleaning pouch system for supporting objects including surgical and non-surgical tools, parts and instruments for pre-soak and ultrasonic cleaning in a water with radio waves, the supporting being done in a safe, convenient and economical manner, the system comprising, in combination:
a sheet of material in a rectangular configuration, the sheet having a linear first side edge and a linear second side edge, the first and second side edges being vertically oriented and parallel with respect to each other, the sheet having a linear first end edge and a linear second end edge, the first and second end edges being horizontally oriented and parallel with respect to each other, a fold line midway between the first and second end edges, the first and second end edges positioned laterally offset from each other and defining an opening between the first and second side edges, the fold line dividing the sheet into a front panel and a superposed rear panel, a chamber formed between the front and rear panels for the receipt of surgical instruments to be cleaned through immersion in a fluid medium, water in the preferred embodiment, with ultrasonic waves;
a primary row of stitching coupling the front and rear panels parallel with and adjacent to each side edge to form a pouch, the primary rows of stitching being formed when the pouch is inverted to be inside out, a secondary row of stitching formed when the pouch is reverted, each secondary row of stitching being parallel with and adjacent to an associated primary row of stitching, each secondary row of stitching being inboard of an associated side edge and an associated primary row of stitching to form a tunnel for an associated side edge and an associated primary row of stitching;
a sliding fastener separably coupling the first and second end edges, the sliding fastener having a slider movable between an open position for allowing objects to be inserted into the chamber and a closed position for securing objects in the chamber during ultrasonic cleaning;
a float fabricated of a buoyant material with a cord coupling the float to the slider, the cord and float adapted to assist a user in retrieving the pouch in the event that the float falls into the fluid medium in which the pouch is being cleaned, the cord being fabricated of a color corresponding to the type of objects in the pouch being cleaned; and
the sheet being fabricated of stainless steel threads, each thread having a diameter of 0.0014 inches, plus or minus 20 percent, the threads being woven with 325 square interstices per square inch, plus or minor 20 percent, the stitching being done with stainless steel threads having a diameter of 0.0014 inches, plus or minus 20 percent.

\* \* \* \* \*